(12) United States Patent
Kumai et al.

(10) Patent No.: US 7,170,289 B2
(45) Date of Patent: Jan. 30, 2007

(54) MAGNETIC RESONANCE IMAGING METHOD AND APPARATUS

(75) Inventors: Hideki Kumai, Chiba (JP); Shinji Kawasaki, Chiba (JP); Hiroyuki Takeuchi, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 24 days.

(21) Appl. No.: 10/503,318

(22) PCT Filed: Jan. 31, 2003

(86) PCT No.: PCT/JP03/00980

§ 371 (c)(1),
(2), (4) Date: Mar. 17, 2005

(87) PCT Pub. No.: WO03/063702

PCT Pub. Date: Aug. 7, 2003

(65) Prior Publication Data

US 2005/0218893 A1    Oct. 6, 2005

(30) Foreign Application Priority Data

Feb. 1, 2002    (JP)    .............................. 2002-025910

(51) Int. Cl.
*G01V 3/00* (2006.01)
(52) U.S. Cl. ...................... 324/309; 324/307
(58) Field of Classification Search ................ 324/309, 324/307, 306
See application file for complete search history.

(56) References Cited

U.S. PATENT DOCUMENTS 6,076,006 A * 6/2000 Van Den Brink et al. .. 600/419

6,331,777 B1    12/2001 Van Den Brink et al.

(Continued)

FOREIGN PATENT DOCUMENTS

| JP | 11-128202 | 5/1999 |
|----|-----------|--------|
| JP | 2000-512533 | 9/2000 |
| WO | WO00/31559 | 6/2000 |

OTHER PUBLICATIONS

Notification Of Transmittal Of Copies of Translation Of The International Preliminary Examination Report (Form PCT/IB/338) and PCT International Preliminary Examination Report (Form PCT/IB/409).

(Continued)

*Primary Examiner*—Louis M. Arana
(74) *Attorney, Agent, or Firm*—Cooper & Dunham LLP (57) ABSTRACT

In diffusion weighted imaging, motion monitoring navigation echoes are measured at every measurement of data after applying an RF excitation pulse, and one of them is set as a reference navigation echo. The reference navigation echo and other navigation echoes are one-dimensionally Fourier-transformed, a linear phase gradient thereof is calculated from those data, a linear phase gradient of the reference navigation echo is compared with those of other navigation echoes, and it is judged whether a difference therebetween is within an acceptable value or not. An echo signal corresponding to a navigation echo having the above difference being larger than the acceptable value is judged that correction based on the navigated motion correction is not applicable therein, and the image is produced by using an echo signal measured along with a navigation echo having the difference being the acceptable value or less. In this manner, a motion component included in the echo signal used for producing the image is made uniform and motion artifacts are eliminated.

20 Claims, 5 Drawing Sheets

U.S. PATENT DOCUMENTS 6,791,323 B2 * 9/2004 Wang et al. ................. 324/309
6,882,150 B2 * 4/2005 Jenniskens et al. ......... 324/309

OTHER PUBLICATIONS

Chinese official action (and English translation thereof) in a corresponding Chinese patent application.

Brockstedt et al., "High-resolution diffusion imaging using phase-corrected segmented echo-planar imaging," Magnetic Resonance Imaging, 2000, vol. 18, No. 6, pp. 649-657.

Anderson et al., "Analysis and Correction of Motion Artifacts in Diffusion Weighted Imaging," Magnetic Resonance in Medicine, 1994, vol. 32, No. 3, pp. 379-387.

* cited by examiner

Fig. 3(b) ⇩ FFT

Fig. 3(c) ⇩ Calcurate Phase (θ)

MAGNETIC RESONANCE IMAGING METHOD AND APPARATUS

TECHNICAL FIELD

The present invention relates to a magnetic resonance imaging method and a magnetic resonance imaging apparatus (hereinafter referred to as MRI apparatus) for obtaining an image in which body movement of an object to be examined is corrected by using a navigation echo, more particularly to an imaging method and apparatus suitable for obtaining a diffusion weighted image reflecting strength of Brownian motion of water molecule in the object's tissue on signal strength.

BACKGROUND OF THE INVENTION

An MRI apparatus is designed to generate a magnetic resonance imaging phenomenon to a nuclear spin in an object to be examined by applying a radio-frequency magnetic field on the object laid in a static magnetic field, measure a nuclear magnetic resonance signal generated inside the object, and process the signal to produce an image.

Imaging techniques of the MRI apparatus include the spin echo method (SE method), a gradient echo method (GE method), an echo planer method (EPI method) based on the SE method or GE method which are used for obtaining a morphological image and a blood flow image of the object, and also include a method used for obtaining an image reflecting strength of Brownian motion of water molecule in the object's tissue. The method for obtaining an image reflecting strength of Brownian motion of water molecule in the object's tissue is referred to as a diffusion weighted imaging method.

The diffusion weighted imaging method suppresses a magnetic resonance signal from a fluent substance inside the object having diffluence such as a water molecule, and thus emphasizes a signal from a portion where the molecule does not move. It is reported that the method is useful for diagnosis of brain infarction, particularly of newly developed brain infarction.

Diffusion weighted imaging based on SE-EPI will be described here. In the SE-EPI, a slicing gradient magnetic field and a 90° RF pulse are first applied to excite a nuclear spin in a slice of the object. Then, the slicing gradient magnetic field is then applied again and a 180° RF pulse is applied to invert the above excited nuclear spin. After applying an offset gradient magnetic field in a phase encoding direction, a readout gradient magnetic field and a phase encoding gradient magnetic field are applied several times at a predetermined time interval, and a plurality of magnetic resonance signals (echo signals) are measured. To perform the diffusion weighted imaging, a pair of gradient magnetic field pulses (diffusion weighted gradient magnetic field pulse) is applied in a desired gradient magnetic field direction before and after the application of 180° RF pulse. By applying the diffusion weighted gradient magnetic field pulse, the echo signal to be measured is provided with diffusion information. The diffusion weighted gradient magnetic field may be applied in one direction, two directions, or three-directions. Thus measured echo signal is reconstructed and a diffusion weighted image is obtained.

By the way, the EPI pulse sequence includes a single-shot EPI in which the nuclear spin is excited once to measure echo signals by the number required for image reconstruction, and a multi-shot EPI in which the nuclear spin is excited several times to measure echo signals by the number necessary for image reconstruction.

It is known that in the MRI apparatus, when the object moves during measurement of a plurality of echo signals, a phase difference occurs among signals generated from the same portion before and after the movement. The same is true of the multi-shot EPI method. Accordingly, when the diffusion weighted imaging is performed using the multi-shot EPI, if the object's body movement is different at each shot, artifacts (hereinafter referred to as motion artifact) are generated in the reconstructed image due to the phase difference occurring among the echo signals.

As a method of correcting the motion artifacts, a motion correction method using navigation echo (hereinafter referred to as navigated motion correction method) is known. In the navigated motion correction method based on the multi-shot SE-EPI, a 90° RF pulse is applied to excite a nuclear spin, a 180° RF pulse is next applied, a gradient magnetic field having a predetermined strength and application time is then applied in a predetermined direction along with a readout gradient magnetic field, and an echo signal for monitoring body movement (navigation echo) is measured. After the navigation echo is measured, a phase encoding gradient magnetic field and a readout gradient magnetic field are repeatedly applied and a plurality of echo signals for imaging (actual measurement) are measured. When a first shot of the above pulse sequence is completed, a second shot, a third shot, . . . an nth shot, . . . and an Nth shot are sequentially performed in a similar manner thereto.

Navigation echo nav(n) and actual echo signals echo(n,m) are thus measured by sequentially executing the first to Nth shots. Here, n represents a shot number of the pulse sequence where $1 \leq n \leq N$, and m represents a measurement number of echo signal in each shot where $1 \leq m \leq M$.

The motion correction of echo signal in the actual measurement is done using thus measured navigation echoes. In the first step of the motion correction, one navigation echo is selected as reference navigation echo $nav_0$ from among above navigation echoes nav(n), ordinarily, the navigation echo of the first shot is selected. In the second step, reference navigation echo $nav_0$ is one-dimensionally Fourier-transformed in the readout direction. Next, in Step 3, navigation echoes other than the reference navigation echo $nav_0$ are also one-dimensionally Fourier-transformed in the readout direction. Furthermore, in Step 4, a phase of data array of the reference navigation echo subjected to Fourier transformation is calculated, phases of data array of other navigation echoes subjected to Fourier transformation are also calculated, and phase difference $\theta(n)$ between the phase of the reference navigation echo then that of other navigation echoes is calculated.

Because calculated phase difference $\theta(n)$ is generated due to a difference between a motion component occurring in measurement of the reference navigation echo and each of those in measurement of other reference navigation echoes, a correction of motion component included in actual echo signal echo (n,m) is executed using phase difference $\theta(n)$ in Step 5.

By executing the above Steps 1 to 5, artifacts caused by the object's movement and included in the actual echo signals obtained by executing the pulse sequence N times are eliminated.

The methods of motion correction using the navigation echo, particularly known as techniques of stably obtaining an image in which motion artifacts are reduced, include a diffusion weighted imaging mentioned in Japanese Unexamined Patent Publication Hei.09-299345 (hereinafter referred to as conventional example 1) and one mentioned in Japanese Unexamined Patent Publication Hei.11-128202 (hereinafter referred to as conventional example 2). In those conventional examples, it is judged using the phase difference whether each of actual echo signals can be corrected or not, and those which cannot be corrected are not used in image reconstruction.

In the diffusion weighted imaging method according to conventional example 1, an average value of phase difference among the plurality of navigation echoes is used as a reference value, and a phase difference between the reference value and a phase value of each navigation echo is calculated. It is judged that the navigated motion correction cannot be performed on a group of actual echo signal acquired in correspondence with a navigation echo having a phase difference larger than an acceptable value, and that navigation echo and actual echo signal are re-collected. In this manner, all actual echo signals for producing an image are made into data which can be properly corrected with the navigated motion correction. Thus, an image with reduced motion artifacts is obtained.

On the other hand, in the diffusion weighted imaging method of conventional example 2, the reference value is an integral value or a peak value calculated from a predetermined navigation echo, or an area or a peak value of a projection pattern obtained by one-dimensionally Fourier-transforming the predetermined navigation echo. Alternatively, an average value of the integral value or the peak value calculated from the predetermined navigation echo, or that of the area or the peak value of a projection pattern obtained by one-dimensionally Fourier-transforming the predetermined navigation echo is used. A value calculated from each navigation echo is compared with the reference value, and it is judged that the navigated motion correction cannot be performed on a group of actual echo signals acquired in correspondence with a navigation echo having a comparison result exceeding an acceptable value. That group of actual echo signals is replaced with another echo signal group or re-collected. In this manner, all of measured echo signals for producing an image are made into data which can be properly corrected with the navigated motion correction. Thus, an image with reduced motion artifacts is obtained.

However, there is a case where sufficient motion correction cannot be performed even with those improved navigated motion correction methods. For example, it is reported in "Analysis and Correction of Motion Artifacts in Diffusion Weighted Imaging] Adam W. Anderson, John C. Gore, MRM 32: 379–387 (1994)" that when the head being an imaging portion of the object moves backward and forward with revolution due to the object's respiration movement during the application of diffusion gradient magnetic field, a linear phase gradient occurs in the phase encoding direction of the imaging area, and so correction effect of the navigated motion correction cannot be expected.

The reason is that the phase value of a navigation echo measured in a state where phase errors vary with respect to the phase encoding direction of the imaging area is an integral value of phases of nuclear spins existing in the phase encoding direction of the imaging area, and so a variation component of phase errors in the phase encoding direction cannot be extracted from that value.

Accordingly, in the both diffusion weighted imaging methods according to conventional example 1 and 2, it is impossible to correctly judge a degree of movement generating the linear phase gradient in the phase encoding direction in the imaging during measurement. Therefore, it is difficult to stably reduce the motion artifacts.

The first object of the present invention is to provide a magnetic resonance imaging method enabling accurate judgment of phase errors including those in a phase encoding direction in the diffusion weighted imaging.

Further, the second object of the invention is to provide an MRI apparatus which can obtain an image in which artifacts generated due to the object's movement are reduced.

SUMMARY OF THE INVENTION

To achieve the above objects, in executing the diffusion weighted imaging, a phase gradient calculated from data obtained by one-dimensionally Fourier-transforming a navigation echo in the readout direction, desirably a linear phase gradient is used as a reference value for judging a degree of phase error of an actual echo occurring due to body movement.

According to research of the inventors of the present invention, when a linear phase gradient occurs in the phase encoding direction in the imaging area due to the object's respiration movement during application of the diffusion gradient magnetic field, a linear phase gradient is almost always generated similarly in the readout direction of the imaging area. Therefore, by using data representing the linear phase gradient in the readout direction as the reference value, the degree of body movement can be properly judged.

Further, in the diffusion weighted imaging method according to the invention, a navigation echo for monitoring body movement is repeatedly acquired at every data measurement after application of the RF excitation pulse, one of those navigation echoes is set to be a reference navigation echo, a linear phase gradient is calculated from data acquired by one-dimensionally Fourier-transforming the reference navigation echo in the readout direction, linear phase gradients of navigation echoes other than the reference navigation echo are also calculated, the linear phase gradient obtained from the reference navigation echo is compared with those obtained from other navigation echoes and it is judged whether the difference therebetween is within an acceptable value or not, it is judged that the navigated motion correction cannot be properly performed on an actual echo signal group corresponding to a navigation echo judged to have a primary gradient of the acceptable value or more, and that navigation echo and actual echo signal are re-collected.

Further, an MRI apparatus according to the invention includes static magnetic field generating means for generating a static magnetic field to a space in which an object to be examined is laid, gradient magnetic field generating means for generating a gradient magnetic field to the space, means for irradiating an RF pulse to the object, means for detecting a nuclear magnetic resonance signal generated from the object, image forming means for producing a tomographic image of the object using the nuclear magnetic resonance signal, and control means for controlling the gradient magnetic field generating means, the RF pulse irradiating means, the detecting means, and the image forming means in accordance with a predetermined pulse sequence, wherein in the pulse sequence provided to the above control means, application of the RF excitation pulse, application of a diffusion gradient magnetic field for reflecting strength of Brownian motion of water molecule in the object's tissue on a signal measured, measurement of the echo signal for monitoring body movement (navigation echo) of the object performed under a fixed phase encoding amount, and measurement of the echo signal used for producing an image are repeatedly performed.

The above control means includes means for judging whether the actual echo obtained by executing the pulse sequence of the navigation echo measurement is available in producing the image or not on the basis of the phase gradient of data acquired by one-dimensionally Fourier-transforming the navigation echoes measured at each application of RF excitation pulses.

More concretely, in the judging means, a reference value is set to be a phase gradient calculated from at least one unit of data acquired by one-dimensionally Fourier-transforming all navigation echoes measured after applying each RF pulse. If difference between the phase gradient of data acquired by one-dimensionally Fourier-transforming a navigation echo and the reference value is within a predetermined range, it is determined that an actual echo signal acquired with the pulse sequence where that navigation echo is measured is not used for producing an image. When there is an actual echo signal not used for producing the image, an actual measurement signal is re-measured at the same phase encoding amount as that of the unused actual echo.

According to the invention, all actual echo signals can be measured while the phase gradient caused by body movement in the application of diffusion gradient magnetic field can be made uniform. Therefore, it is possible to suppress motion artifacts and stably provide an image.

BEST MODE FOR CARRYING OUT THE INVENTION

Hereinafter, embodiments of the present invention will be described with reference to the drawings.

Figure 1:
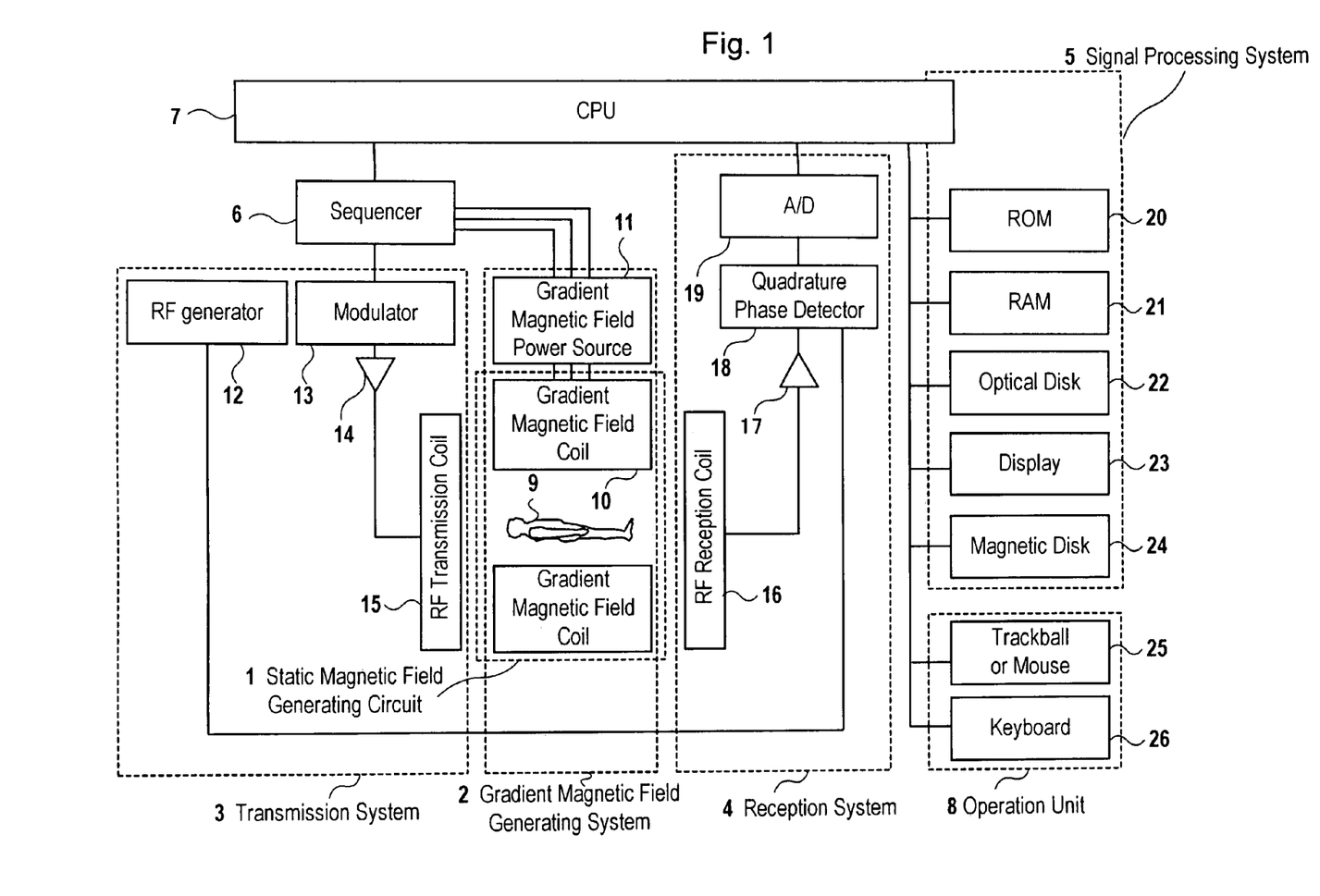
FIG. 1 is a block diagram showing schematic structure of an MRI apparatus according to the invention.

FIG. 1 is a block diagram showing a schematic structure of an MRI apparatus according to the invention. As shown in FIG. 1, the MRI apparatus includes static magnetic field generator 1, gradient magnetic field generating system 2, transmission system 3, reception system 4, signal processing system 5, sequencer 6, central processing unit (CPU) 7, and operation unit 8.

Static magnetic field generator 1 is designed to generate a uniform static magnetic field having a predetermined strength to a space of a predetermined size with which object 9 can be inserted in a longitudinal direction of the object or in a direction perpendicular thereto, including a permanent magnet, or a resistive magnet, or a superconductive magnet.

Gradient magnetic field generating system 2 includes gradient magnetic field coil 10 for generating gradient magnetic fields in X-, Y-, and Z-directions, and gradient magnetic field power source 11 for supplying current to each of coils generating the gradient magnetic fields in the three directions. Gradient magnetic field generating system 2 drives the gradient magnetic field power source of the coil in response to a command output from sequencer 6 mentioned later, and thus applies to object 9 the gradient magnetic fields Gs, Gp, and Gr respectively in the slicing direction, the phase encoding direction, and the readout direction. Positions and directions of a slicing plane of object 9 can be freely set with application manners of gradient magnetic fields. Further, gradient magnetic field generating system 2 is further designed to generate a diffusion gradient magnetic field for reflecting strength of Brownian motion of water molecule in the object's tissue on signal strength in the diffusion weighted imaging. The diffusion gradient magnetic field may be applied to any one, two, or all of the gradient magnetic fields in the three directions.

Transmission system 3 is designed to irradiate an RF pulse to generate nuclear magnetic resonance to atomic nuclei constructing body tissue of object 9 in response to a command output from sequencer 6, including RF generator 12, modulator 13, RF amplifier 14, and RF transmission coil 15. In transmission system 3, an RF pulse signal output from RF generator 12 is modulated by modulator 13, the modulated signal is amplified by RF amplifier 14, the amplified RF signal is supplied to transmission coil 15, and an RF pulse being an electromagnetic wave is thus irradiated from the transmission coil to object 9.

Reception system 4 is designed to detect an echo signal (NMR signal) irradiated due to a nuclear magnetic resonance phenomenon from the atomic nuclei of body tissue constructing object 9, including RF reception coil 16, amplifier 17, quadrature phase detector 18, and A/D converter 19. In reception system 4, an electromagnetic wave (NMR signal) generated from the tissue of object 9 in response to the electromagnetic wave irradiated to the object by transmission coil 15 is detected by reception coil 16 arranged close to object 9, the NMR signal is amplified by amplifier 17, the amplified signal is subjected to quadrature detection in quadrature detector 18, made into two series of signals of a sin component and a cos component and input into A/D converter 19, and the two series of analog signals input into A/D converter 19 are converted into digital signals and transmitted to signal processing system 5.

Signal processing system 5 is designed to perform signal processings such as image reconstruction calculation using the NMR signal detected by reception system 4, make the result into an image, and display it on a display device, including CPU 7 for performing processings such as Fourier transformation, correction coefficient calculation, and image reconstruction calculation on the NMR signal and controlling sequencer 6, ROM 20 for storing a program for time-sequentially performing image analysis processing and a parameter used for execution thereof, RAM 21 for temporarily storing the measurement parameter, the NMR signal detected by reception system 4, and images used for setting a region of interest (ROI), and storing a parameter for setting the ROI, optical disk 22 and magnetic disk 24 being a data storing unit for storing data of an image reconstructed by CPU 7, and display 23 being a display unit for imaging the image data read out from the data storing unit and displaying it as a tomographic image.

Sequencer 6 is control means for executing a predetermined pulse sequence for measuring the NMR signal from the body tissue of object 9, which works under the control of CPU 7 and transmits various commands necessary for collection of the tomographic data of object 9 to transmission system 3, gradient magnetic field generating system 2, and reception system 4. The sequencer of the MRI apparatus according to the present invention is installed a pulse sequence for the diffusion weighted imaging including the application of diffusion gradient magnetic field 107 and the measurement of navigation echo 110.

Operation unit 8 is designed to input control information for processings performed by signal processing system 5, including trackball/mouse 25, keyboard 26, and the like.

Figure 2:
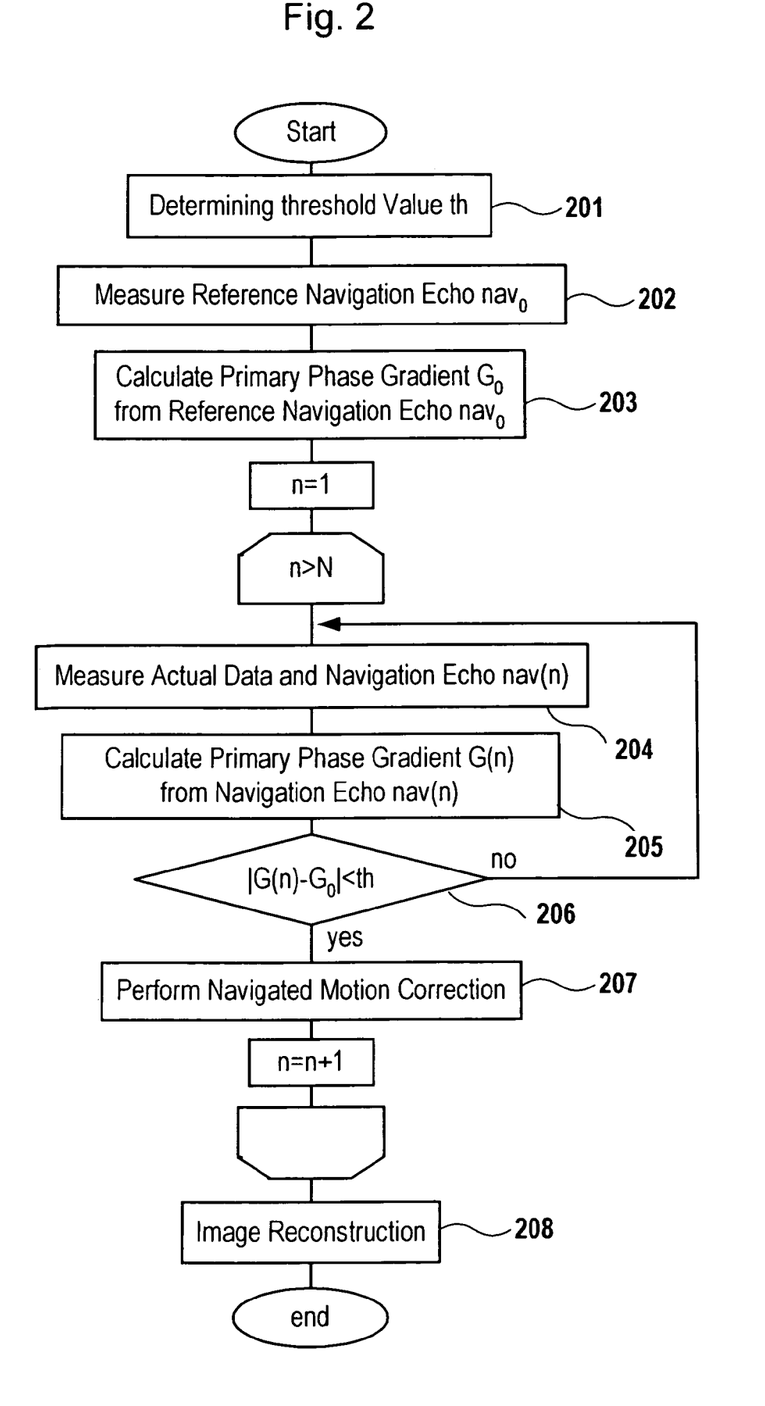
FIG. 2 is a flow chart of a process of diffusion weighted imaging according to one embodiment of the invention.
Figure 5:
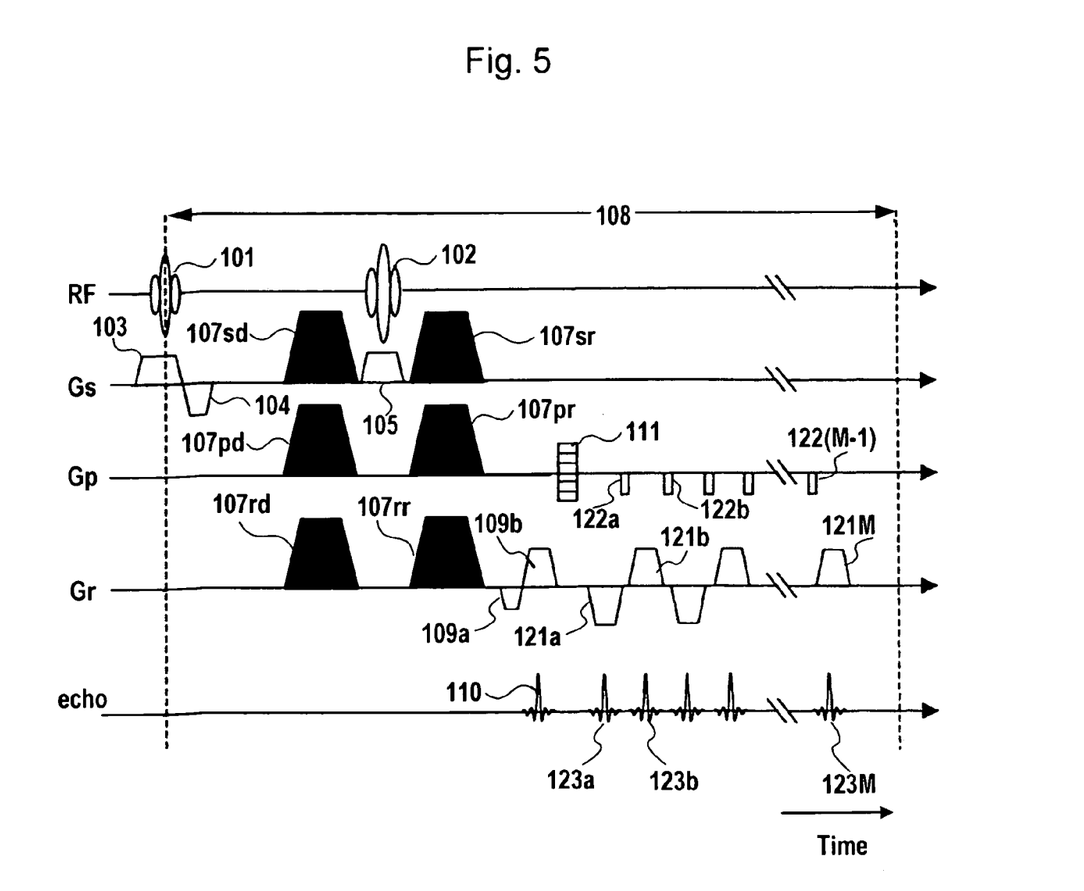
FIG. 5 is a diagram showing one example of a pulse sequence of diffusion weighted imaging including measurement of navigation echo.

Next, the diffusion weighted imaging performed by using the MRI apparatus constructed as above will be described with reference to FIG. 2 and FIG. 5. FIG. 2 is a flow chart showing a process of the diffusion weighted imaging according to the invention, which is programmed and stored into CPU 7. FIG. 5 shows an example of a pulse sequence performing the diffusion weighted imaging stored in sequencer 6. This pulse sequence is a diffusion weighted imaging pulse sequence based on the SE-EPI. Prior to execution of this pulse sequence, execution of the diffusion weighted imaging is selected and input into operation unit 8 by an operator, and threshold th is set for judging whether an actual echo signal is used in image reconstruction or not (Step 201). Threshold th may be set by the operator before beginning measurement, or it also may be prepared in advance as a fixed value in the apparatus. Threshold th works as an acceptable value of a difference with the reference value for making uniform the phase gradients of all actual echoes in the phase encoding direction, which may be determined by finding the phase gradient experientially or with simulation and setting a concrete value on the basis of this phase gradient. Alternatively, an acceptable difference may be set in percent figure.

Prior to imaging, i.e. execution of the pulse sequence shown in FIG. 5, the position of a portion to be imaged of object 9 is determined by moving a bed (not shown) in a uniform static magnetic field space (measurement space) generated by the static magnetic field generator. A longitudinal direction of the object and a direction perpendicular thereto are respectively set as a phase encoding direction and a readout direction in imaging.

Before starting the actual measurement, reference navigation echo $nav_0$ is measured (Step 202). The measurement of navigation echo $nav_0$ may be execution of the pulse sequence shown in FIG. 5 in which offset phase encoding gradient magnetic field pulse 111 is a predetermined offset amount, e.g. zero, or may be execution of the pulse sequence shown in FIG. 5 without applying offset phase encoding gradient magnetic field 111 and phase encoding gradient magnetic field pulse 121.

Reference navigation echo $nav_0$ measured is stored into a memory of CPU 7, read out, and one-dimensionally Fourier-transformed in the readout direction. From the one-dimensionally Fourier-transformed data a linear phase gradient is calculated. Thus calculated phase gradient is set as reference value $G_0$ in a step described below (Step 203). Meanwhile, it is also preferable to repeat Step 202, acquire a plurality of navigation echoes $nav_0$, and set an average value of the linear phase gradients calculated therefrom as reference value $G_0$.

Figures 3A, 3B, 3C:
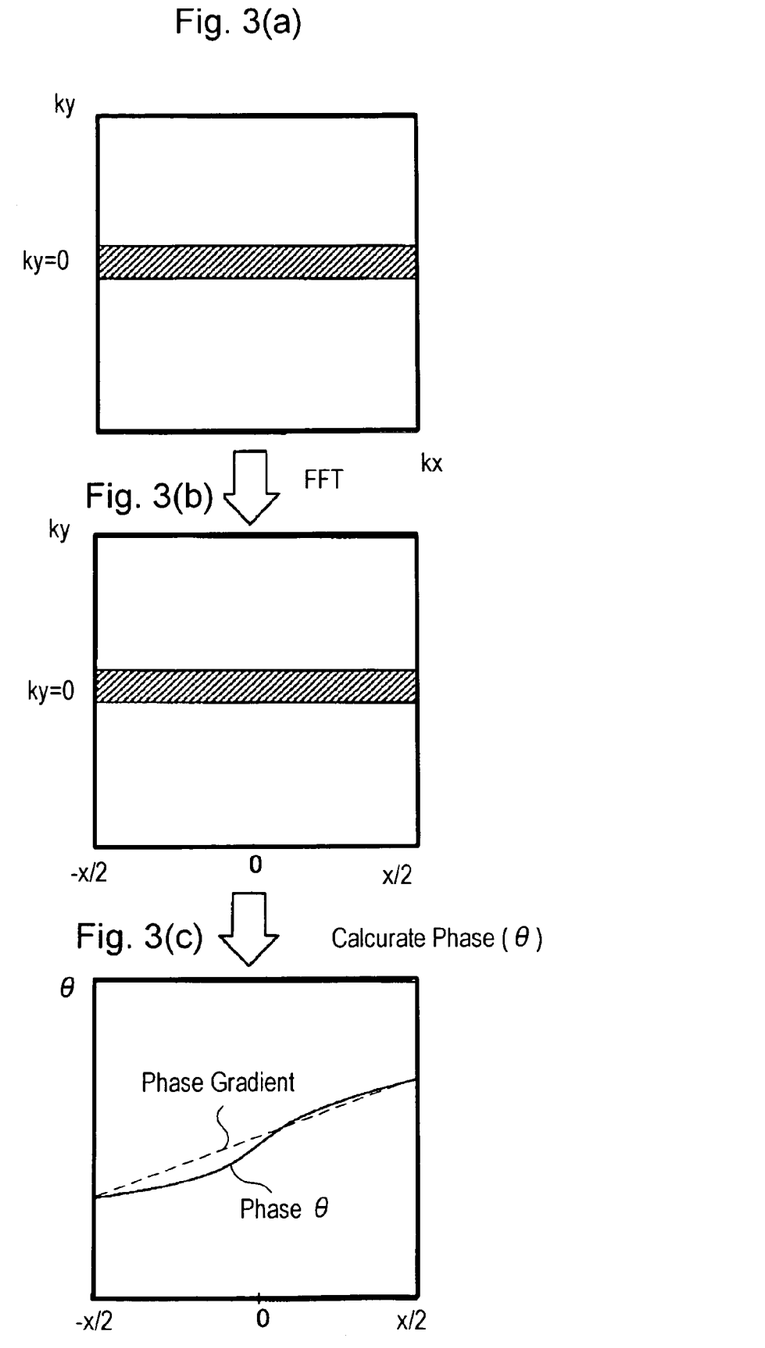
FIG. 3 is a diagram illustrating a process of calculating a phase gradient from a navigation echo.

Next, a calculation method of the linear phase gradient will be described with reference to FIG. 3. Reference navigation echo $nav_0$ shown in FIG. 3(a) is read out and its data (complex data) array is one-dimensionally Fourier-transformed as shown in FIG. 3(b). A phase value is calculated by using an arctangent of a ratio between a real part and an imaginary part of each of data, and an array of phase value $\theta$ is calculated in the readout direction (x direction) shown in FIG. 3(c). The phase value array in the readout direction is, e.g. fitted into a linear function using a least square method so as to calculate the phase gradient shown with a broken line in the figure. The phase gradient may be calculated with another method, i.e. in a simple manner in which phase value difference $\Delta\theta$ between two arbitrary points in the x direction of the field of view (FOV) is divided by distance x of the FOV in the x direction and set thus calculated $\Delta\theta/x$ as linear phase gradient G. The calculation method of linear phase gradient is programmed and stored into CPU 7.

After thus calculating reference value $G_0$, the diffusion weighted imaging is started. The imaging may be started with input of the operator or automatically started by CPU 7. As the imaging is started, CPU 7 sequentially transmits a command to sequencer 6 to generate the gradient magnetic field, the RF pulse, and receive the signal in accordance with time series of the pulse sequence shown in FIG. 5. Sequencer 6 controls gradient magnetic field generating system 2, transmission system 3, and reception system 4 in response to the command from CPU 7 and executes the pulse sequence of FIG. 5.

First, slicing gradient magnetic field 103 is applied to object 9, while RF excitation pulse 101 having a frequency corresponding to a slice position imaged and a band corresponding to a slice thickness. Thus, the nuclear spin of object 9 in the imaging slice is excited by 90° from the static magnetic field direction. When excitation is finished, slicing gradient magnetic field 104 having an opposite polarity and a half application amount of slicing gradient magnetic field 103 is applied, and rephasing of the nuclear spin in the slicing direction is performed.

Next, first diffusion gradient magnetic fields 107sd, 107pd, and 107rd having a predetermined strength and application time are applied respectively in the slicing, phase encoding, and readout directions. As those first diffusion gradient magnetic fields are applied, the excited nuclear spin is made to perform precession movement in the respective directions in accordance with magnetic field strength corresponding to positions, and thus the nuclear spins are dephased.

After that, 180° RF pulse 102 and slicing gradient magnetic field 105 are applied to invert the nuclear spin excited by RF excitation pulse 101.

After inverting the nuclear spin, second diffusion gradient magnetic fields are applied symmetrically to the first diffusion gradient magnetic fields with respect to RF pulse 102. Second diffusion gradient magnetic fields 107sr, 107pr, and 107rr are applied respectively in the slicing, phase encoding, and readout directions. Respective gradient magnetic fields 107sr, 107pr, and 107rr are applied temporally symmetrically to the first diffusion gradient magnetic fields, and with the same strength, application time, and polarity as those of the first diffusion gradient magnetic fields. The second diffusion gradient magnetic field rephases the nuclear spin dephased by the first diffusion gradient magnetic field in combination with the operation of the 180° RF pulse. If the nuclear spin in the object moves during the interval between applications of the first diffusion gradient magnetic field and the second gradient magnetic field, the phase of the moving nuclear spin does not return in its moving direction even when the second diffusion gradient magnetic field is applied, and it is not measured in subsequent measurement of echo signal (actual echo signal). As a result, in the actual measurement, a signal from the nuclear spin of molecule constituting object 9 which performs Brownian motion, such as water, are suppressed and a signal from the nuclear spin of tissue which does not move is emphasized. Accordingly, the first and second diffusion gradient magnetic fields are referred to as Motion Probing Gradient Magnetic Field, hereinafter abbreviated as MPG.

When application of MPG 107 is finished, navigation echoes being echo signals for monitoring body movement are measured by applying gradient magnetic fields 109a and 109b in the readout direction. Those readout gradient magnetic fields 109a and 109b are applied to measure navigation echo nav(1) 110. In the measurement of navigation echo according to the present embodiment, an application amount of the phase encoding gradient magnetic field is zero. The navigation echo nav(1) 110 received and measured by reception system 4 are stored into a memory of CPU 7.

Subsequently to the measurement of navigation echo 110, phase encoding gradient magnetic field 111 is applied. An application amount of phase encoding gradient magnetic field 111 corresponds to an offset value for determining a position of starting to store the actual echo signals measured afterward in a phase direction (ky direction) in the k space.

Subsequently, readout gradient magnetic fields 121a, 121b, ... 121M and phase encoding gradient magnetic fields 122a, 122b, ... 122(M−1) are applied and actual echo signals 123a, 123b, ... 123M are measured. The actual echo signal is sampled by A/D converter 19 of reception system 4 the number of times corresponding to a pixel value in the readout direction of the image and stored into an address corresponding in the ky direction of the k space.

After the measurement of echo signal 123M is completed, i.e. one pulse sequence is completed, it is judged whether the actual echo signal can be used for producing an image or not. In this judgment processing, measured navigation echo nav(1) 110 is first read out, one-dimensionally Fourier-transformed in the readout direction, and linear phase gradient G(1) is calculated with the above described manner (Step 205).

Next, absolute value D(1) of a difference between the calculated linear phase gradient G(1) and reference value $G_0$, and absolute value D(1) of the difference is compared with threshold value th set in Step 201. When the threshold value is set to be an acceptable difference to the reference value in percentage figures, a proportion of absolute value D(1) of the difference with reference value $G_0$ is calculated in percentage figures and compared. If the comparison result is D(1)≦th, actual echo echo(1,m) is available in image reconstruction and its data are held.

If the comparison result is D(1)>th, however, it is judged that actual echo echo(1,m) is not used in image reconstruction. In this case, actual echo signal echo(1,m) and navigation echo nav(1) are void, processings from Step 204 are performed again using the pulse sequence of repetition number 1, and processings of Steps 204 to 206 are repeated until it is judged that the actual echo signals is available in image reconstruction.

In the judgment processing of step 206, when it is judged that the actual echo signal is used in image reconstruction, echo signal echo (1,m) is subjected to phase correction using navigation echo nav(1) 110 measured in the same pulse sequence (Step 207). The phase correction can be performed on the basis of the navigated motion correction method mentioned in the section of conventional technique. That is, a phase value of reference navigation echo $nav_0$ in the readout direction is set as a reference value, a phase difference at each position in the readout direction between the reference phase value and the phase value of navigation echo nav(1) 110 is calculated, phase correction is performed on echo(1,m) measured by using the phase difference in the readout direction with the pulse sequence where its naviga-tion echo nav(1) 110 is measured, and thus effects caused by body movement is eliminated.

After that, the pulse sequence shown in FIG. 5 is repeatedly performed (N−1) times with preset time of repetition (TR) 108. The repetition number (N−1) is determined by dividing the pixel number in the phase direction of the image to be obtained by number M of the actual echo signal measured during one pulse sequence. At each repetition, the offset value of phase encoding gradient magnetic field 111 is modified.

In this manner, the pulse sequence shown in FIG. 5 is executed N times in total to measure navigation echo nav(n) (n is in the range from 1 to N) and actual echo signal echo(n,m) (n is in the range from 1 to N and m is in the range from 1 to M). (That is, the navigation echoes of N in number and the actual echo signals of N×M in number are measured.) Navigation echo nav(n) and actual echo signal echo (n,m) measured by repeating the pulse sequence are subjected to the processings of Steps 204 to 207 of FIG. 2, and eventually, a group of actual echo signals is acquired which are given all phase encoding amount necessary for producing one image and subjected to the motion correction. Image reconstruction is performed on the echo signal group utilizing two-dimensional Fourier transformation, and a diffusion weighted image is thus obtained.

In thus obtained image, the motion component which cannot be corrected with the known navigated motion correction (i.e., motion components caused by respiration of the object during MPG application) are made uniform of all echo signals used in the image, and so the motion component does not appear on the image as an artifact. Therefore, image quality is improved.

The above is the description of one embodiment of the present invention, in which Steps 204 to 206 are repeatedly executed until it is judged that the actual echo signals measured at each execution of the pulse sequence is available in image reconstruction. However, the invention is not limited thereto and modification may be made. The following is the description of the modification.

Figure 4:
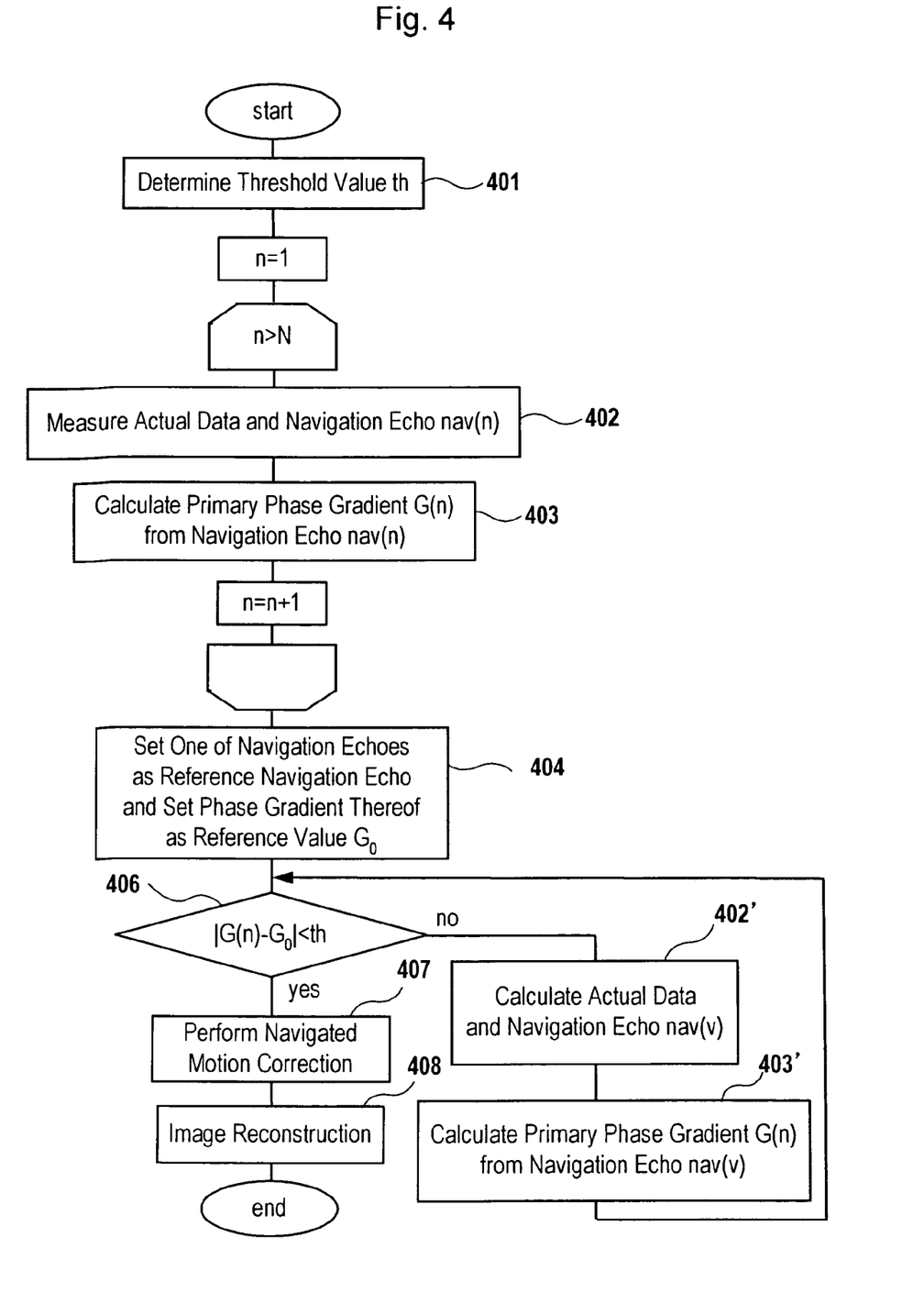
FIG. 4 is a flow chart showing a process of diffusion weighted imaging according to another embodiment of the invention.

According to the modified embodiment of the invention, the pulse sequence is first executed for all repetition number n, and after actual echo signal echo(n,m) and navigation echo nav(n) necessary for producing one image are measured, the judgment step is executed. FIG. 4 shows the process of this modified embodiment.

In the example shown in FIG. 4 too, threshold value th is first set in a manner similar to the embodiment shown in FIG. 2 (Step 401). After threshold value th is set, reference navigation echo is not independently measured. The pulse sequence shown in FIG. 5 is executed for repetition number n being 1 to N and navigation echo nav(n) and actual echo signal echo(n,m) are measured (Step 402). As Step 402 is executed, actual echo signals of a phase encoding number necessary for producing one image and navigation echoes of N in number are measured.

Next, each of the navigation echoes of N in number is Fourier-transformed in the readout direction, and linear phase gradient G(n) is calculated from the Fourier-transformed data (Step 403). Reference value $G_0$ is set on the basis of calculated phase gradient G(n) (Step 404).

Reference value $G_0$ set in Step 404 may be minimum phase gradient G(n) or an average value of linear phase gradients calculated for a plurality or all of navigation echo nav(n). Further, it may be a linear phase gradient having a minimum difference to the average value among linear phase gradients G(n) calculated for navigation echoes nav(n).

When reference value $G_0$ is determined, a difference between linear phase gradient $G(n)$ of navigation echo nav(n) measured with the pulse sequence of repetition number n and reference value $G_0$ is calculated, and it is judged whether the difference is predetermined threshold value th or less or not (Step 406). If phase gradient $G(n)$ of navigation echo nav(n) of repetition number n excesses threshold value th, the actual echo signal measured with the pulse sequence of the repetition number n of that navigation echo is not used in image reconstruction. If it is the threshold or less, the actual echo signal measured with the pulse sequence of the repetition number n of that navigation echo is used in image reconstruction.

Actual echo signal echo(n,m) of repetition number n judged to be not used in image reconstruction is re-collected by repeatedly executing Steps 402', 403', and 406, and echo signals necessary for reconstructing one image are eventually acquired.

All of the echo signals acquired are subjected to the motion correction based on the conventional technique (Step 407), and the echo signals subjected to the motion correction are two-dimensionally Fourier-transformed and an image is reconstructed (Step 408). The reconstructed diffusion weighted image is displayed on display 23.

According to the above described embodiments, in Step 206 or 406 the actual echo signal is re-measured until it is judged that the actual echo signal measured may be used in image reconstruction. However, that process might greatly prolong the measurement time. Accordingly, it is effective to limit in advance the repetition number of measurement. If no actual echo signal is available in image reconstruction among those measured within the limited number of repetition, an actual echo signal measured with a pulse sequence in which a navigation echo is closest to the reference value may be selected for image reconstruction. This method also reduces motion artifacts greater than in the conventional technique.

In the above embodiments of the invention, the diffusion weighted imaging is performed with a pulse sequence based on SE-EPI. However, the invention is also applicable to a diffusion weighted imaging based on GE-EPI.

According to the above described invention, the motion correction is performed using the navigation echo in the diffusion weighted imaging while body movement is identified by using a linear phase gradient calculated from the data one-dimensionally Fourier-transformed in the readout direction. Accordingly, it is possible to judge a degree of the object's body movement causing the linear phase gradient in the phase encoding direction.

Using the linear phase gradient it is judged whether an actual echo signal measured with a pulse sequence where the navigation echo is acquired is used in image reconstruction or not. If the actual echo signal is judged to be not available, it is re-collected. Thus, it is possible to correct all actual echo signals used for reconstructing one image with the navigated motion correction. Therefore, motion artifacts are suppressed and a good diffusion weighted image is reconstructed by using the actual echo signal corrected with the navigated motion correction.

The invention claimed is:

1. A magnetic resonance imaging method comprising the steps of:
    (a) setting a reference value for judging whether or not an imaging echo signal measured is used in image reconstruction;
    (b) exciting a nuclear spin in an object to be examined laid in a uniform static magnetic field by applying a slicing gradient magnetic field and an RF excitation pulse;
    (c) executing measurement of motion monitoring navigation echo obtained by applying a phase encoding gradient magnetic field of a predetermined amount, and subsequently executing measurement of imaging echo signal obtained by sequentially applying phase encoding gradient magnetic fields of various phase encoding amounts;
    (d) one-dimensionally Fourier-transforming the navigation echo detected in Step (c) and calculating a linear phase gradient thereof from the acquired data; and
    (e) comparing the calculated linear phase gradient with the reference value and judging a degree of the object's body movement on the basis of difference therebetween.

2. A magnetic resonance imaging method according claim 1, further comprising the steps of:
    (f) using the imaging echo signal in image reconstruction only when the object's body movement is judged to be small; and
    (g) re-measuring the imaging echo signal when the object's body movement is judged to be considerable.

3. A magnetic resonance imaging method comprising the steps of:
    (a) setting a threshold value for judging whether or not an imaging echo signal measured is available in image reconstruction;
    (b) exciting a nuclear spin of an object to be examined by applying a slicing gradient magnetic field and an RF excitation pulse and measuring a reference navigation echo for monitoring motion;
    (c) calculating a linear phase gradient from the reference navigation echo;
    (d) measuring a navigation echo obtained by applying a phase encoding gradient magnetic field of a predetermined amount, and subsequently measuring an imaging echo signal obtained by applying phase encoding gradient magnetic fields of various phase encoding amounts;
    (e) one-dimensionally Fourier-transforming the navigation echo measured in Step (d) and calculating a linear phase gradient in from the acquired data; and
    (f) comparing the calculated linear phase gradient with the linear phase gradient of the reference navigation echo and judging a degree of the object's body movement from the difference therebetween and the threshold value.

4. A magnetic resonance imaging method according to claim 3, further comprising the steps of:
    (g) using the imaging echo signal in image reconstruction only when the object's body movement is judged to be small; and
    (h) re-measuring the imaging echo signal when the object's body movement is judged to be considerable.

5. A magnetic resonance imaging method comprising the steps of:
    (a) positioning an object to be examined in a uniform static magnetic field;
    (b) exciting a nuclear spin in the object to be examined by applying a slicing gradient magnetic field and an RF excitation pulse;
    (c) applying a motion probing gradient magnetic field to the excited nuclear spin;

(d) measuring a motion monitoring navigation echo obtained by applying a phase encoding gradient magnetic field of a predetermined amount;

(e) measuring an imaging echo signal obtained by sequentially applying phase encoding gradient magnetic fields of various phase encoding amounts;

(f) repeating a pulse sequence including above Steps (b) to (e) a plurality of number of times;

(g) one-dimensionally Fourier-transforming each navigation echo detected in Step (d) in a readout direction and calculating a linear phase gradient of each of the acquired data;

(h) determining one of the calculated linear phase gradients as a reference value, calculating differences between the reference value and other linear phase gradients, and judging a degree of body movement by comparing those differences with a predetermined threshold value;

(i) performing motion correction by subtracting the difference from the echo signal in which body movement is judged to be small in Step (h); and (j) performing image reconstruction by two-dimensionally Fourier-transforming the echo signals subjected to the motion correction.

6. A magnetic resonance imaging method according to claim 5, further comprising a step of:

(k) judging that an echo signal measured with a pulse sequence which measured a navigation echo including body movement judged to be considerable in Step (h) is not used in image reconstruction.

7. A magnetic resonance imaging method according to claim 5, further comprising a step of:

(I) re-collecting the echo signal judged to be not used in image reconstruction in Step (k) by executing above Steps (d) and (e).

8. A magnetic resonance imaging method comprising the steps of:

(a) positioning an object to be examined in a uniform static magnetic field (b) exciting a nuclear spin in the object by applying a slicing gradient magnetic field and an RF excitation pulse;

(c) measuring a motion monitoring navigation echo obtained by applying a phase encoding gradient magnetic field of a predetermined amount;

(d) one-dimensionally Fourier-transforming the navigation echo measured in Step (c) in the readout direction and determining a reference value for judging a degree of body movement by calculating a linear phase gradient using data thereof to judge;

(e) exciting the nuclear spins in the object by applying a slicing gradient magnetic field and an RF excitation pulse, and applying a motion probing gradient magnetic field in a predetermined direction;

(f) detecting a motion monitoring navigation echo obtaining by a phase encoding gradient magnetic field of a fixed amount;

(g) measuring imaging echo signals obtained by sequentially applying phase encoding gradient magnetic fields of various phase encoding amount;

(h) repeating a pulse sequence including above Steps (e) to (g) a plural times;

(i) one-dimensionally Fourier-transforming each of navigation echoes detected in Step (f) and calculating a linear phase gradient thereof; and (j) calculating differences between the linear phase gradients and the reference value set in Step (d) and judging a degree of the object's body movement by comparing those differences.

9. A magnetic resonance imaging method comprising the steps of:

(a) setting a reference value for judging whether or not an imaging echo signal measured is used in image reconstruction;

(b) exciting a nuclear spin in an object to be examined laid in a uniform static magnetic field by applying a slicing gradient magnetic and an RF excitation pulse;

(c) executing measurement of motion monitoring navigation echo obtained by applying a phase encoding gradient magnetic field of a predetermined amount, and subsequently executing measurement of imaging echo signal obtained by sequentially applyng phase encoding gradient magnetic fields of various phase encoding amounts;

(d) one-dimensionally Fourier-transforming the navigaiton echo detected in Step(c) and calculating a linear phase gradient thereof from the acquired data; and (e) comparing the calculated linear phase gradient with reference value and detecting the revolving movement of and examined region of the object using the linear phase gradient information of the navigation echo.

10. A magnetic resonance imaging apparatus comprising:

a static magnetic field generating means for generating a uniform static magnetic field to a space where an object to be examined is laid;

gradient magnetic field generating means for generating a gradient magnetic field to the space;

means for irradiating an RF pulse to the object;

means for detecting an echo signal generated from the object;

image producing means for producing a tomographic image of the object by using the echo signal;

control means for controlling the gradient magnetic field generating means, the RF pulse irradiating means, and the detecting means to repeatedly perform application of the RF excitation pulse, application of a motion probing gradient magnetic field for reflecting strength of Brownian motion of water molecule in the object's tissue on strength of signals measured, measurement of a navigation echo of the object under a fixed phase encoding amount, and measurement of the echo signals used for producing the image;

means for judging whether or not an actual echo obtained by executing a pulse sequence containing the navigation echo measurement is available in producing the image on the basis of phase gradient of data obtained by one-dimensionally Fourier-transforming the navigation echo measured at every application of RF pulse; and means for re-collecting the actual echo signal judged to be unavailable in producing the image by the judging means.

11. a magnetic resonance imaging apparatus according to claim 10, further comprising means for re-collecting the actual echo signal judged to be unavailable in producing the image by the judging means.

12. A magnetic resonance imaging apparatus comprising:

a static magnetic field generating means for generating a uniform static magnetic field to a space where an object to be examined is laid;

gradient magnetic field generating means for generating a gradient magnetic field to the space;

RF pulse irradiating means for irradiating an RF pulse to the object;

detecting means for detecting an echo signal generated from the object;

image producing means for producing a tomographic image of the object by using the echo signal;

control means for controlling the gradient magnetic field generating means, RF pulse irrradiating means to measure a navigation echo and echo signals used for producing an image after application of a motion probing gracdient magnetic field for reflecting strength of Brownian motion of water molecule in the object's tissue; and a detecting means for detecting a movement of an examined region of the object by using a linear phase gradient information of the navigation echo.

13. A magnetic resonance imaging apparatus according t claim 12, wherein the detecting means is a revolving movement detecting means which detects the revolving movement of the examined region of the object.

14. A magnetic resonance imaging apparatus according to claim 13, wherein the magnetic resonance imaging apparatus comprises a storage means for storing a threshold value to compare with the linear phase gradient, and a judging means to judge a degree of the revolving of the object comparing the linear phase gradient and the threhold value.

15. A magnetic resonance imaging apparatus according to claim 14, wherein the magnetic resonance imaging apparatus comprises an input means for inputting the threshold value by an operator.

16. A magnetic resonance imaging apparatus according to claim 14, wherein the magnetic resonance imaging apparatus comprise a means for calculating the threshold value based on a reference navigation echo measured before starting the actual measurement.

17. A magnetic resonance imaging apparatus according to claim 13, wherein the revolving movement detecting means detect the movement of the head of the object.

18. A magnetic resonance imaging apparatus according to claim 17, wherein the revolving movement detecting means detects the revolving movement of the head in the backward and forward direction.

19. A magnetic resonance imaging apparatus according to claim 12, wherein the linear phase gradient information is obtained by calculating the gradient of the data which is obtained by one-dimensional Fourier transformation of the navigation echo.

20. A magnetic resonance imaging apparatus according to claim 12, wherein the magnetic resonance imaging apparatus comprises a means for executing phase correction of echo information used for producing an image, based on phase information obtained by the navigation echo.

* * * * *